United States Patent [19]

Golden et al.

[11] 4,440,170

[45] Apr. 3, 1984

[54] SURGICAL CLIP APPLYING INSTRUMENT

[75] Inventors: Donald Golden, Cherry Hill; Robert B. Duncan, Bridgewater, both of N.J.

[73] Assignee: Ethicon, Inc., Somerville, N.J.

[21] Appl. No.: 18,073

[22] Filed: Mar. 6, 1979

[51] Int. Cl.³ ............................................ A61B 17/12
[52] U.S. Cl. .................................... 128/325; 128/321
[58] Field of Search .................. 128/325, 321, 334 R, 128/337, 335; 29/243.56; 72/410

[56] References Cited

U.S. PATENT DOCUMENTS

| | | | |
|---|---|---|---|
| 2,968,041 | 1/1961 | Skold | 128/335 |
| 3,439,522 | 4/1969 | Wood | 72/410 |
| 3,518,993 | 7/1970 | Blake | 128/321 |
| 3,777,538 | 12/1973 | Weatherly et al. | 128/325 X |
| 3,828,791 | 8/1974 | Santos | 128/321 |
| 3,954,108 | 5/1976 | Davis | 128/325 |
| 4,064,881 | 12/1977 | Meredith | 128/325 |

*Primary Examiner*—Michael H. Thaler
*Attorney, Agent, or Firm*—Robert L. Minier

[57] ABSTRACT

A pistol-type surgical instrument for applying ligating clips to blood vessels and other tubular ducts in remote locations which are substantially inaccessible to conventional forceps-type appliers. Tubular jaw assemblies of various lengths may be mounted on the pistol-grip handle of the instrument, and the mounted jaw assembly is fully rotatable to permit orientation of the clip applying jaws. The jaws are preferably at right angles to the axis of the tubular jaw assembly, but may be slanted forward or rearward up to about 20 degrees.

25 Claims, 10 Drawing Figures

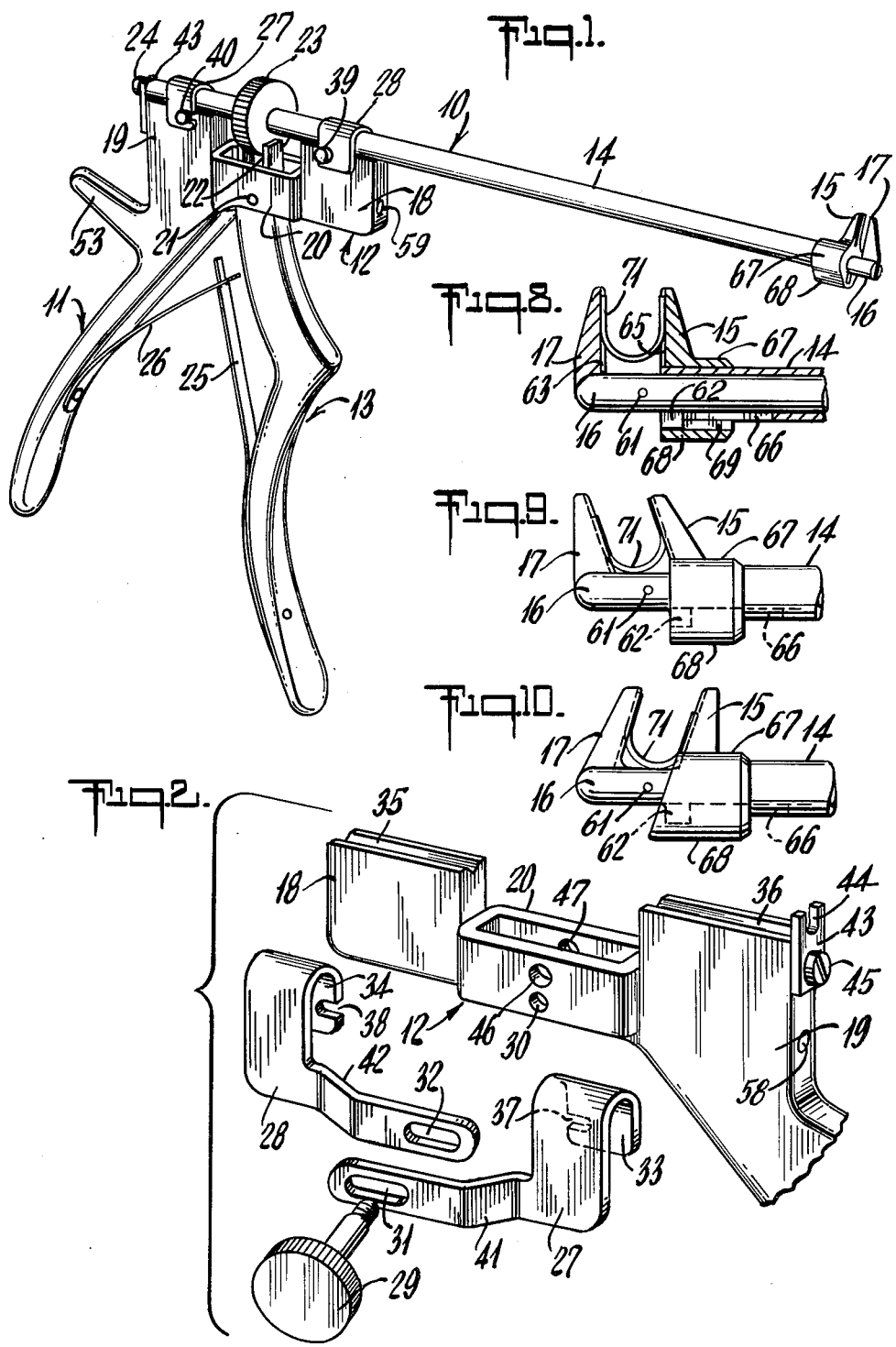

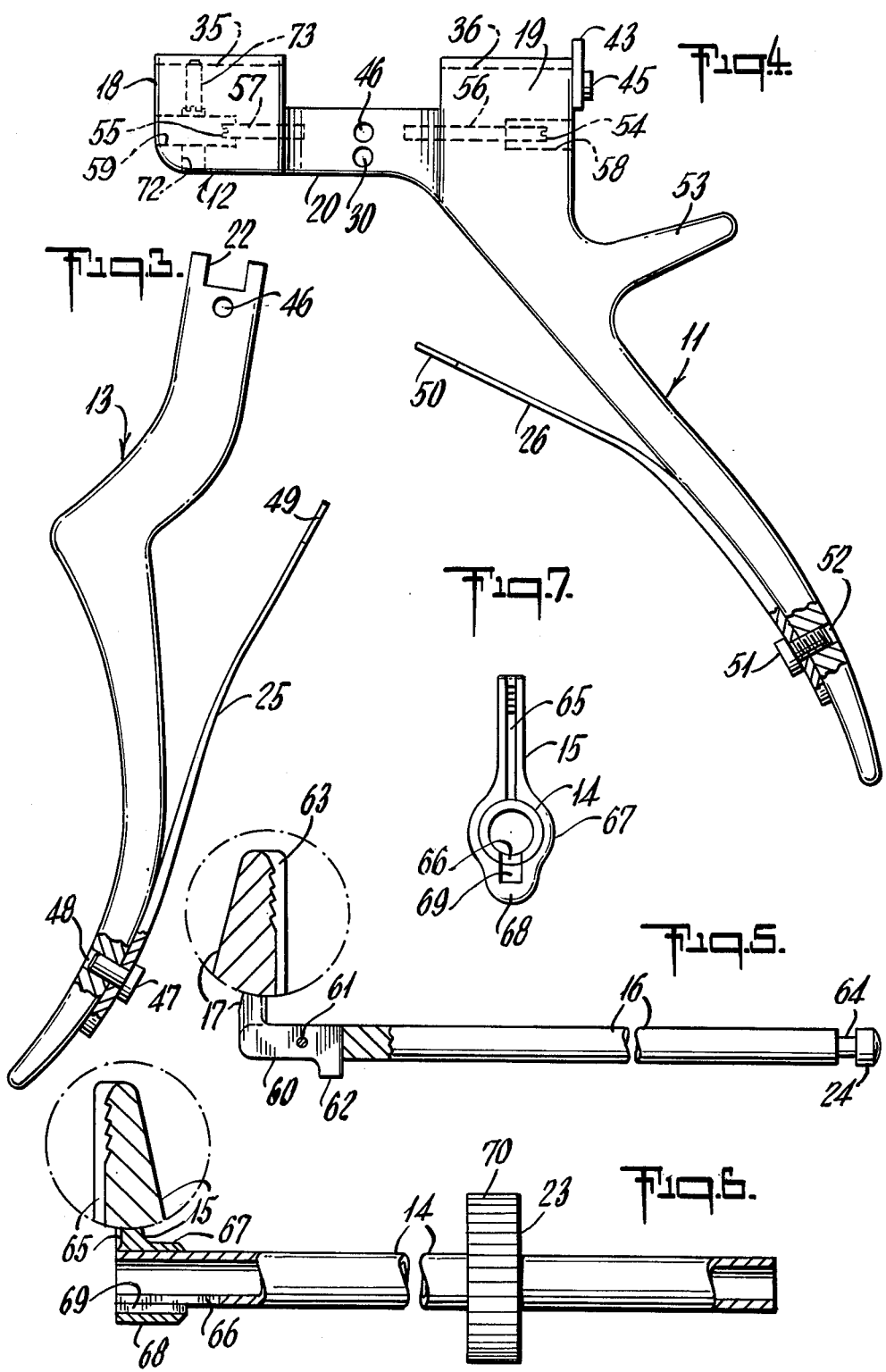

SURGICAL CLIP APPLYING INSTRUMENT

BACKGROUND OF THE INVENTION

This invention relates to a hemostatic clip applier, and, more particularly, to a pistol-type applier having an elongated tubular jaw assembly able to reach areas inaccessible to conventional forcep-type instruments.

In the course of a surgical operation, it is usually necessary to sever blood vessels which must be quickly clamped or ligated to prevent excessive bleeding which could interfere with the operation and pose unnecessary risks to the patient. While major blood vessels are temporarily clamped and later rejoined when the wound is closed, many severed vessels of the vascular system are permanently closed either because other vessels are available to serve their function, or because that portion of the anatomy being served by the vessel has been surgically removed.

Severed vessels are conventionally closed by either tying with ligatures or clamping with ligating clips. Ligating clips are often preferred, especially for permanent closure because of the ease and speed of placement, and the security of the closure. Clips are conventionally applied by means of a forceps-type applier as described, for example, in U.S. Pat. No. 3,439,522. These appliers work well in most general procedures where the severed vessel is accessible to the instrument. In certain procedures, however, particularly in otologic surgery or neurosurgery, a relatively small hole is made in the skull in order to reach and clip off certain blood or other vessels therein, and the small hole does not admit to the use of the forceps-type applier. In thoracic surgery, fluid ducts deep within the chest cavity are difficult to reach with a forceps-type instrument without disturbing other organs. For these and other specific applications, the surgeon may use a special applier having a long, slender nose such as that described in U.S. Pat. Nos. 3,518,993 or 3,777,538.

The long-nose surgical clip applicators of the prior art have certain disadvantages which are overcome by means of the present invention. In prior art applicators, the angle of the jaws holding the clip are fixed relative to the handles of the instrument so that the entire instrument must be maneuvered to align the clip with the vessel. Moreover, the length of the jaw assemblies of the prior art appliers are either permanently mounted or not readily changed so that the surgeon may often be forced to use a longer and more awkward instrument than necessary.

It is accordingly an object of the present invention to overcome the above and other disadvantages of the prior art instruments by providing a long-nose surgical clip applicator having a fully rotatable jaw member. It is a further object of this invention to provide a ligating clip applier with readily interchangeable jaw members of various lengths, and with jaws set at various angles to the main axis of the instrument. These and other objects of the present invention will be apparent from the ensuing description and claims.

SUMMARY

The surgical clip applier of the present invention comprises a stationary handle member and a movable trigger member pivotally connected thereto, and an elongated tubular jaw assembly comprising tube and rod members rotatably secured to the stationary handle member and having opposing jaws on the distal ends thereof. The tube member is engaged by the upper extremity of the trigger member by means of which the tube member and jaw on the distal end thereof are made to reciprocate in an axial direction. The rod member extends through and is slidable within the tube member. The proximal end of the rod member is rotatably but axially fixed to the stationary handle member so that as the tube member is reciprocated by the action of the trigger member, the rod member is stationary and the jaws at the distal ends of the tube and rod members are made to open and close. Sliding guide means between the tube and rod members are provided in the vicinity of the jaws to maintain the jaws in constant alignment during rotation and opening and closing. A knurled ring secured to the tube member is effectively engaged by a yoke at the upper extremity of the trigger member and provides a convenient means for rotating the tubular jaw assembly in order to orient the position of the jaws.

The trigger member of the applier is biased away from the stationary handle member by spring means which causes the jaws of the applier to be maintained in a normally open 30 position. The spacing between the fully open jaws is adjusted to receive and hold a ligating clip. With the clip in position, the nose of the instrument may be inserted into the surgical field and the jaws rotated to any desired angle relative to the handles of the instrument. When the clip is in position over the vessel to be ligated, the trigger member is squeezed toward the stationary handle member thereby closing the jaws and setting the clip on the the vessel. Relaxing the force on the trigger member allows the jaws to open and the instrument to be withdrawn for reloading with another clip.

The tubular jaw assembly is mounted to the stationary handle member by quick release catches which allow jaw assemblies of different lengths to be easily exchanged with no secondary adjustment to the instrument. The jaw assemblies may be provided in any desirable length, and the jaws at the distal end thereof may be set at right angles to the axis of the tubular jaw assembly or slanted forward or rearward by up to about 20 degrees.

DESCRIPTION OF DRAWINGS

FIG. 1 is a view in perspective from the right forward quadrant of a surgical clip applicator in accordance with the present invention.

FIG. 2 is an exploded, partial view in perspective from the left rearward quadrant of the instrument of FIG. 1 showing the barrel mounting and latching means.

FIG. 3 is a left plan view of the trigger member of the instrument of FIG. 1.

FIG. 4 is a left plan view of the stationary handle member of the instrument of FIG. 1.

FIG. 5 is a foreshortened left plan view in partial cross section of the rearward facing jaw and rod assembly of the instrument of FIG. 1 with the jaw detail enlarged.

FIG. 6 is a foreshortened left plan view in partial cross section of the forward facing jaw and tube assembly of the instrument of FIG. 1 with the jaw detail enlarged.

FIG. 7 is an enlarged end view of the forward facing jaw and tube assembly of FIG. 6.

FIG. 8 is a partial sectional view of the jaw assembly of the instrument of FIG. 1 with a surgical clip engaged therein.

FIG. 9 is a plan view of the jaw assembly of an instrument of the present invention wherein the jaws are slanted forward with a surgical clip engaged therein.

FIG. 10 is a plan view of the jaw assembly of an instrument of the present invention wherein the jaws are slanted rearward with a surgical clip engaged therein.

DESCRIPTION OF PREFERRED EMBODIMENTS

With reference to FIG. 1, there is shown a pistol-grip-type surgical clip applicator of the present invention comprising stationary handle member 11 including horizontal tubular jaw mounting section 12 at the upper end thereof, trigger member 13 pivotally mounted to said handle member at said tubular jaw mounting section, and tubular jaw assembly 10 mounted on said tubular jaw mounting section and comprising tube 14 terminating in forward facing jaw 15 at the distal end thereof and rod 16 extending through said tube 14 and terminating in rearward facing jaw 17 at the distal end thereof.

Tubular jaw mounting section 12 includes a pair of spaced-apart cradles 18 and 19 and an intermediate box member 20 adapted to receive the upper extremity of trigger member 13. Trigger member 13 is pivotally mounted by pin 21 to said tubular jaw mounting section 12 with the upper extremity of said trigger member extending within box member 20. The upper extremity of trigger member 13 terminates in yoke 22 which is adapted to engage ring 23 secured to tube 14 at a position approximately centered over box 20 and intermediate cradle members 18 and 19. The lower extremity of trigger member 13 is biased away from handle member 11 by cooperating leaf springs 25 and 26.

Tube 14 is slidably and rotatably mounted in saddles 18 and 19 of barrel mounting section 12 by means best illustrated in FIG. 2. Tubular jaw retainers 27 and 28 are secured to box 20 of tubular jaw mounting section 12 by means of thumb screw 29 which extends through drill hole 46 in one wall of box 20 and is secured in tapped hole 47 in the opposing wall of box 20. Retainers 27 and 28 are provided with slot openings 31 and 32 respectively to receive thumb screw 29 and allow for lateral displacement of the retainers. Retainers 27 and 28 are additionally provided with inverted, U-shaped sections 33 and 34 having an effective open width slightly larger than the outside diameter of tube 14.

Tube jaw assembly 10 is mounted to stationary handle 11 as illustrated in FIG. 1 by positioning tube 14 in V-shaped grooves 35 and 36 of saddles 18 and 19, and positioning the U-shaped sections of retainers 27 and 28 over tube 14. When the retainers are in position, inward facing open slots 37 and 38 of retainers 27 and 28 are aligned with pins 39 and 40 extending from saddles 18 and 19 as illustrated in FIG. 1, and the retainers are locked in position by moving the retainers so that pins 39 and 40 are engaged by slots 37 and 38. The retainers are thereafter secured against further movement by tightening thumb screw 29. Retainers 27 and 28 are offset at 41 and 42 to accommodate the width of box 20 and allow both legs of U-shaped sections 33 and 34 to fit closely against the walls of saddles 18 and 19.

Also illustrated in FIG. 2 is rod retaining bracket 43 having vertical open slot 44 adapted to engage a corresponding circumferential groove in the proximal end of rod 16 when the assembly of rod 16 and tube 14 is mounted on saddles 18 and 19. Bracket 43 is permanently secured to the end of saddle 19 by screw 45. Drill hole 30 further illustrated in FIG. 2 receives trigger pivot pin 21 in a press fit. A corresponding drill hole in the opposite wall of box 20 is visible in FIG. 1.

FIGS. 3 and 4 are detailed views of trigger member 13 and handle member 11 respectively. In FIG. 3, trigger member 13 is shaped for comfortable grasping by the fingers of the surgeon. At the upper extremity of trigger member 13 is yoke 22 and pivot hole 46. Leaf spring 25 is secured to the lower extremity of trigger member 13 by means of screw 47 and drilled and tapped hole 48. The free end of leaf spring 49 is slotted to provide a tongue and groove engagement with free end 50 of cooperating leaf spring 26 as illustrated in FIG. 1.

Referring now to FIG. 4, stationary handle member 11 has drilled and tapped hole 52 at the lower extremity thereof whereby leaf spring 26 is secured to handle member 11 by means of screw 51. Handle 11 is shaped to comfortably fit the heel of the hand of the surgeon, and projection 53 defines the upper limit of the grasping area of the handle.

Integral with the upper portion of handle 11 is tubular jaw mounting section 12 which is illustrated in detail in FIG. 4, and includes, in addition to the features already described, set screws 54 and 55 which are threaded through drilled and tapped holes 56 and 57 in saddles 18 and 19, and extend into the interior of box 20. The set screws function to limit the travel of yoke 22 of trigger member 13 in both directions to control the travel of jaw 15 when opening and closing as explained hereinafter. Drill holes 56 and 57 are countersunk at 58 and 59 to provide access to the heads of set screws 54 and 55.

FIG. 5 illustrates rod member 16 partially sectioned at the distal end to show the construction of jaw 17. Rod 16 is slotted at the distal end to receive horizontal extension 60 of jaw 17 in a tongue and groove relationship. Jaw 17 is secured in the slot of rod 16 by means of pin 61. Rod 16 is keyed to tube 14 by means of flange 62 which extends from the horizontal extension of jaw 17 and, in cooperation with the structure of barrel 14 as hereinafter described, functions to maintain jaw alignment during rotation of the jaw assembly and when opening or closing the jaw.

The proximal end of rod 16 includes circumferential groove 64 which cooperates with slot 44 of bracket 43 illustrated in FIG. 2 to prevent axial movement of rod 16 while permitting free rotation when the tubular jaw assembly is mounted on the instrument as shown in FIG. 1.

Referring now to FIG. 6, there is shown a partially sectioned and foreshortened view of tube 14. On the distal end of tube 14 is mounted outward facing jaw 15 which includes at its base cylindrical section 67 circumscribing tube 14 and permanently secured thereto. Tube 14 is slotted at 66 to accommodate flange 62 of jaw 17 illustrated in FIG. 5, and cylinder 67 is provided with slotted flange guard 68 to enclose flange 62 of jaw 17 in the complete tubular jaw assembly as illustrated in FIG. 8.

Referring further to FIGS. 5 and 6, jaws 15 and 17 are provided with grooves 65 and 63 respectively on the faces thereof to receive and hold a single surgical clip as best illustrated in FIG. 8. Grooves 63 and 65 preferably contain serrations on the distal ends thereof as illustrated in the enlarged views of FIGS. 5 and 6 to enhance the ability of the jaws to grip and hold the clip during manipulation of the instrument and closure of the clip over the vessel being ligated.

The construction of jaw 15 will be more fully understood by reference to FIG. 7 where tube 14 and jaw 15 are shown in end view. Flange guard 68 is an extension of cylinder 67, and contains slot 69 having a width and depth corresponding to the width and depth of flange 62. Tube 14 includes slot 66 aligned with slot 69 and extending a short distance beyond cylinder 67 to accommodate the full travel of flange 62. It should be noted that flange guard 68 is a desirable, but not essential feature of the present invention and might be eliminated for certain applications where it is desirable to reduce the overall diameter of the distal tip of the clip applicator.

Returning now to FIG. 6, ring 23 is secured to tube 14 intermediate saddles 18 and 19 and at a point approximately centered over box 20 when the tubular jaw assembly is mounted on the instrument as illustrated in FIG. 1. Ring 23 is preferably knurled on the outer surface 70 thereof to facilitate rotation of the tube in the assembled instrument.

FIG. 8 illustrates the detail of the tubular jaw assembly comprising rod 16 inserted within tube 14 with jaws 15 and 17 in alignment and with clip 71 retained between the jaws in grooves 63 and 65.

The operation of the surgical clip applier of FIG. 1 is generally as follows: a tube and rod jaw assembly is selected and mounted to the stationary handle member of the instrument as aforedescribed to obtain the instrument as illustrated in FIG. 1. The trigger member biasing springs cause the yoke of the trigger member to urge ring 23 and tubular member 14 in a rearward direction, thereby opening the jaws of the instrument. Set screw 54 is adjusted to obtain the appropriate spacing between jaws 15 and 17 to accommodate clip 71 with a friction fit. The mounted tubular jaw assembly may be freely rotated about 360 degrees by means of knurled ring 23. Flange 62 of jaw 17 in cooperation with slot 66 of tube 14 serves to maintain the jaws in alignment as tube 14 is rotated.

After the jaw assembly has been rotated to place the jaws at the desired angle, the instrument is manipulated to place the clip over the vessel to be ligated, and the trigger member is squeezed to close the jaws and set the clip. As the trigger is urged toward the stationary handle member against the bias of the springs, the yoke of the trigger member urges ring 23 and barrel 14 forward, thereby closing jaw 15 against jaw 17. Rod 16 is restrained against axial travel by circumferential groove 64 cooperating with slot 44 of bracket 43, and jaw 17 accordingly remains stationary as jaw 15 closes toward it.

The forward travel of jaw 15 is limited by set screw 55 abutting yoke 22, and set screw 55 is adjusted before use to provide for complete clip closure without placing unnecessary stress on the jaws of the instrument. After the clip has been set, the pressure on the trigger member is relaxed allowing the biasing springs to move the trigger member forward, thereby opening the jaws of the instrument by moving tubular member 14 and jaw 15 in a rearward direction while jaw 17 remains stationary.

Once set screws 54 and 55 have been adjusted for a given clip, other tubular jaw assemblies of longer or shorter lengths may be mounted on the handle member with no readjustment of the instrument being required for the same 30 size clip. In the event a larger or smaller clip is to be applied, readjustment of the set screws to obtain the appropriate jaw spacing for the new clip may be required.

The rotational freedom of jaw assembly 10 on saddles 18 and 19 is controlled by frictional engagement with nylon-tipped set screw 73 which projects from drill hole 72 into V-shaped groove 35 of saddle 18 as illustrated in FIG. 4. After the jaw assembly is mounted on saddles 18 and 19 and retainers 27 and 28 have been secured as aforedescribed, set screw 73 is adjusted so that the nylon tip abuts the wall of tube 14. Set screw 73 is thereupon tightened until the frictional engagement with tube 14 is sufficient to secure the jaw assembly in any desired position while permitting the intentional rotation thereof with minimal effort.

For certain surgical procedures, it may be desirable to angle the jaws in a forward or rearward direction as illustrated in FIGS. 9 and 10. The jaws may be angled up to about 20 degrees or more from the vertical and still operate in a satisfactory manner. Clips set from angled jaws tend to roll during closure with the result that the legs of the clip are of unequal lengths when closed, but this has no practical consequence in terms of efficacy or performance. Jaws 15 and 17 may be slanted forward or rearward up to about 45 degrees or even more with the understanding that the greater the slant, the greater the roll imparted to the clip during closure.

The preceding description has been directed toward a preferred embodiment of the present invention as illustrated in FIG. 1. Many variations in design and construction will be apparent to those skilled in the art, and are included within the scope of the present invention. For example, the cooperating leaf springs of the handle of the instrument may be replaced by any other means effective to bias the trigger member away from the stationary handle member so that the jaws of the instrument are in a normally open position. In addition, a variety of mechanisms are available for mounting the tubular jaw assembly onto the handle member, the only requirement being that the tubular member is free to rotate with sufficient axial movement to permit the jaws to open and close. Likewise, the rod member of the applier may be mounted in any manner which allows the rod to rotate freely without axial movement.

In other embodiments, jaw 17 may be secured to rod 16 by a pin as shown or may be welded or silver-soldered in place. Likewise, jaw 15 may be secured to tube 14 by any convenient means. The cooperating flange and slot assembly of jaws 15 and 17 may be replaced by any other guide means effective to maintain the jaws in alignment during rotation and closure.

We claim:

1. A surgical clip applicator comprising
   a handle member;
   a pair of spaced-apart cradles integral with said handle member at one end thereof;
   a trigger member pivotally connected to said handle member and extending into the space between said cradles;
   an elongated tubular jaw assembly rotatably mounted on said cradles, said jaw assembly comprising an axially movable tube member having a forward facing jaw on the distal end thereof and a rod member extending through said tube member and having a rearward facing jaw on the distal end thereof;
   means on said tube member intermediate said cradles engaging said trigger member;

means on the proximal end of said rod member restraining said rod member from movement in an axial direction while permitting rotation thereof;

means aligning said forward facing and rearward facing jaws, said jaws being axially movable but nonrotatable with respect to each other; and means for rotating said mounted tubular jaw assembly with said jaws in alignment.

2. An applicator of claim 1 wherein said trigger member terminates in a yoke extending into the space between said cradles.

3. An applicator of claim 2 wherein said yoke of said trigger member engages a ring secured to and extending from said tube member of said jaw assembly.

4. An applicator of claim 1 wherein said trigger member is biased away from said handle member in a normally open position.

5. An applicator of claim 1 wherein said rod member is restrained from axial movement by means of a circumferential groove therein engaging a cooperating slot extending from said handle member.

6. An applicator of claim 1 wherein said forward and rearward facing jaws are aligned by means of a flange extending from said rod member into a cooperating slot in said tubular member.

7. An applicator of claim 1 wherein said forward and rearward facing jaws are at right angles to the axis of said tubular jaw assembly.

8. A surgical clip applicator comprising
a handle member;
a pair of spaced-apart cradles integral with said handle member at one end thereof;
a trigger member pivotally connected to said handle member and extending into the space between said cradles;
an elongated tube member rotatably and slidably mounted on said pair of cradles and having a forward facing jaw on the distal end thereof;
means on said tube member intermediate said pair of cradles engaging said trigger member;
an elongated rod member extending through said tube member having a rearward facing jaw on the distal end thereof;
means on the proximal end of said rod member restraining said rod member from movement in an axial direction while permitting rotation thereof;
means aligning said forward facing and rearward facing jaws, said jaws being axially movable but nonrotatable with respect to each other; and
means for rotating said mounted tube and rod members as a unit with said jaws in alignment.

9. An applicator of claim 8 wherein said trigger member terminates in a yoke extending into the space between said cradles.

10. An applicator of claim 9 wherein said yoke of said trigger member engages a ring secured to and extending from said tube member.

11. An applicator of claim 8 wherein said trigger member is biased away from said handle member in a normally open position.

12. An applicator of claim 8 wherein said rod member is restrained from axial movement by means of a circumferential groove therein engaging a cooperating slot extending from said handle member.

13. An applicator of claim 8 wherein said forward and rearward facing jaws are aligned by means of a flange extending from said rod member into a cooperating slot in said tubular member.

14. An applicator of claim 8 wherein said forward and rearward facing jaws are at right angles to the axis of said tubular jaw assembly.

15. An applicator of claim 8 wherein said forward and rearward facing jaws are angled up to about 20 degrees from vertical relative to the axis of said tubular jaw assembly.

16. A surgical clip applicator comprising
a handle member;
a pair of spaced-apart cradles integral with said handle member at one end thereof;
a trigger member pivotally connected to said handle member and extending into the space between said cradles;
first and second stop means limiting the travel of said trigger member relative to said handle member;
means for biasing said trigger member against said first stop means away from said handle member in a normally open position;
an elongated tube member rotatably and slidably mounted on said pair of cradles and having a forward facing jaw on the distal end thereof;
means on said tube member intermediate said pair of cradles engaging said trigger member;
an elongated rod member extending through said tube member having a rearward facing jaw on the distal end thereof;
means on the proximal end of said rod member restraining said rod member from axial movement while permitting rotation thereof;
means aligning said forward facing and rearward facing jaws, said jaws being axially movable but nonrotatable with respect to each other; and
means for rotating said mounted tube and rod members as a unit with said jaws in alignment, said jaws being normally biased apart by said trigger member a first predetermined distance according to said first stop means, and closing to a second predetermined distance according to said second stop means as said trigger member is urged toward said handle member and against said second stop means.

17. An applicator of claim 16 wherein said trigger member terminates in a yoke extending into the space between said cradles.

18. An applicator of claim 17 wherein said yoke of said trigger member engages a ring secured to and extending from said tube member.

19. An applicator of claim 16 wherein said rod member is restrained from axial movement by means of a circumferential groove therein engaging a cooperating slot extending from said handle member.

20. An applicator of claim 16 wherein said forward and rearward facing jaws are aligned by means of a flange extending from said rod member into a cooperating slot in said tubular member.

21. An applicator of claim 16 wherein said first and second stop means comprise set screws extending through said cradles and into the space between said cradles.

22. An applicator of claim 16 wherein said jaws are biased apart a first predetermined distance corresponding to the width of a surgical clip.

23. An applicator of claim 16 wherein said jaws close to a second predetermined distance corresponding to the thickness of a closed surgical clip.

24. An applicator of claim 16 wherein said forward and rearward facing jaws are at right angles to the axis of said tubular jaw assembly.

25. An applicator of claim 16 wherein said forward and rearward facing jaws are angled up to about 20 degrees from vertical relative to the axis of said tubular jaw assembly.

* * * * *